United States Patent [19]

Rossiter

[11] 4,181,437
[45] Jan. 1, 1980

[54] APPARATUS FOR EXAMINING THE INFRARED SPECTRUM OF SMALL QUANTITIES OF MATERIALS IN THE VAPOR PHASE

[76] Inventor: Valentine J. Rossiter, 16 Rathmore Ave., Kilmacud, Stillorgan, Co. Dublin, Ireland

[21] Appl. No.: 770,865

[22] Filed: Feb. 22, 1977

[30] Foreign Application Priority Data

Feb. 25, 1976 [IE] Ireland ............................... 367/76

[51] Int. Cl.² ........................................... G01N 1/00
[52] U.S. Cl. .................................. 356/246; 250/343; 356/36
[58] Field of Search .................... 356/36, 246; 250/343

[56] References Cited

U.S. PATENT DOCUMENTS 3,120,608  2/1964  Bird ...................................... 250/343
3,843,257  10/1974  Wooten ................................. 356/36

OTHER PUBLICATIONS

Gas & Liquid Chromatography Abstracts 1970, Edited Knapman et al., Inst. of Petroleum, 1971, p. 199.
High-Temp .... Cell for Infrared Studies ..., Kagel et al., Applied Spectroscopy, vol. 21 #3, May/Jun. 67, pp. 187-188.

*Primary Examiner*—Vincent P. McGraw
*Attorney, Agent, or Firm*—Sughrue, Rothwell, Mion, Zinn and Macpeak

[57] ABSTRACT

The invention provides a spectral analysis cell for the batch spectroscopic analysis of materials. The cell incorporates an integral trapping chamber whereby a sample may be trapped in any conventional manner in for example a sample trapping tube and delivered to the trapping chamber where it can be vaporized so as to deliver a vapor from the sample trapping tube to the interior of the cell.

3 Claims, 11 Drawing Figures

APPARATUS FOR EXAMINING THE INFRARED SPECTRUM OF SMALL QUANTITIES OF MATERIALS IN THE VAPOR PHASE

BACKGROUND OF THE INVENTION

Introduction

The present invention relates to a cell and method for the spectral analysis of materials in the gas or vapour state.

FIELD OF THE INVENTION

In British Patent Specification No. 1,282,357 there is described a spectral analysis cell for gases or vapours comprising a hollow body, a window in the body consisting of an opening through which gas or vapour can flow out and optical radiation can pass, an inlet to the body for gas or vapours to be analysed and means for causing a curtain of inert gas to flow across the opening. There are many such constructions of cell for the batch spectroscopic analysis of materials.

Similarly, U.S. Pat. No. 3,490,850 describes a cell for the continuous analysis by photometric and spectrophotometric measurements.

It will be appreciated that the infrared analysis of a gas chromatographic fraction that is to say, the combination of gas, chromatography and infrared spectroscopy is one of the most important methods of separating a complex mixture into its components and then identifying or characterising each of them.

It has however been found with the cells such as those referred to above that the problems of collecting and preparing the fraction for infrared analysis are so difficult that it has become the practice to supply extremely complicated and sophisticated in-line analysis equipment. Needless to say such in-line analysis equipment is relatively expensive and costs considerably more than two basic items of equipment required namely the chromatograph and the spectrometer both of which are fairly standard equipment in most laboratories.

Since the transfer of samples form the chromatograph to the spectometer has proved difficult the batch infrared analysis of gas chromatographic fractions has not heretofore been particularly successful.

OBJECTS

The present invention is directed towards providing an improved construction of spectral analysis cell.

Another object of the invention is to provide a spectral analysis cell which is readily adapted to batch analysis.

A further object of the invention is to provide a spectral analysis cell that does not require expensive support equipment.

A still further object of the invention is directed towards providing a method of batch spectral analysis of materials.

SUMMARY OF THE INVENTION

This invention provides in a spectral analysis cell for the spectroscopic analysis of materials:

an integral trapping chamber for reception of a trapped sample;
means communicating between the trapping chamber and the interior portion of the cell; and
means for vapourizing the trapped sample within the trapping chamber to deliver a vapour from the trapped sample into the interior of the cell.

Further the invention provides a method of making a spectral analysis of a solid, liquid, or gaseous material in vapour or gaseous form including the steps of:

trapping a sample;
introducing the sample into a trapping chamber integral with and communicating with a spectral analysis cell;
vapourising the sample or part thereof in the trapping chamber to cause the vapourised sample to occupy the interior portion of the cell; and
spectroscopically analysing the vapourised sample in the cell.

The invention will be more clearly understood from the following description of some preferred embodiments thereof given by way of example only with reference to the accompanying drawings in which.

Figure 2:
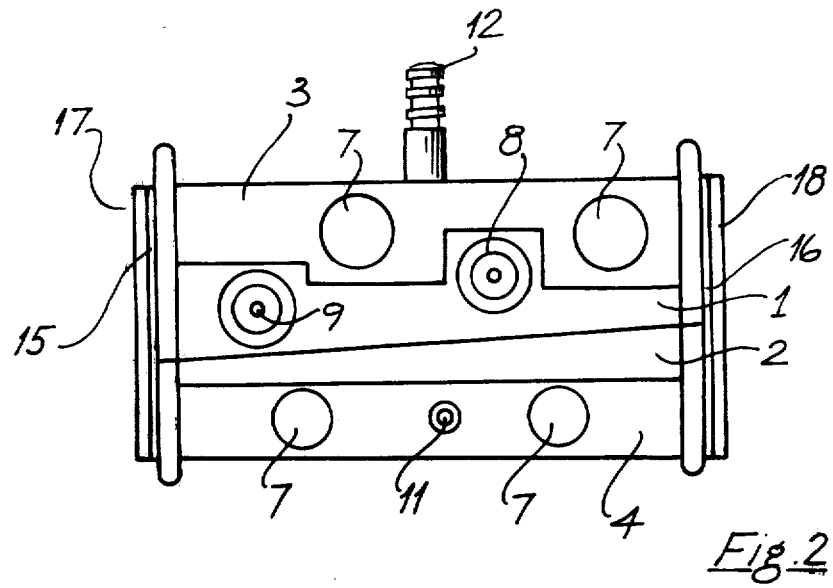
FIG. 2 is a plan view of portion of the cell with some of the parts removed.
Figure 1:
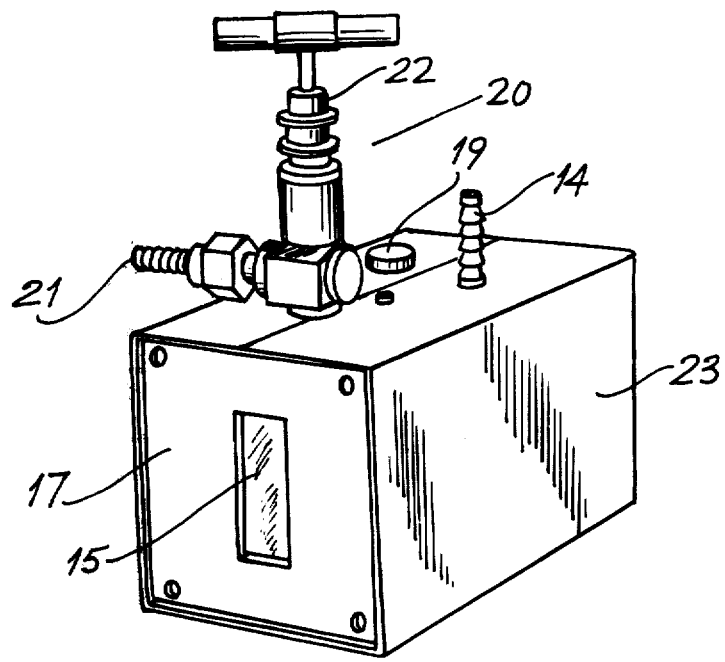
FIG. 1 is a perspective view of a cell according to the invention.
Figure 3:
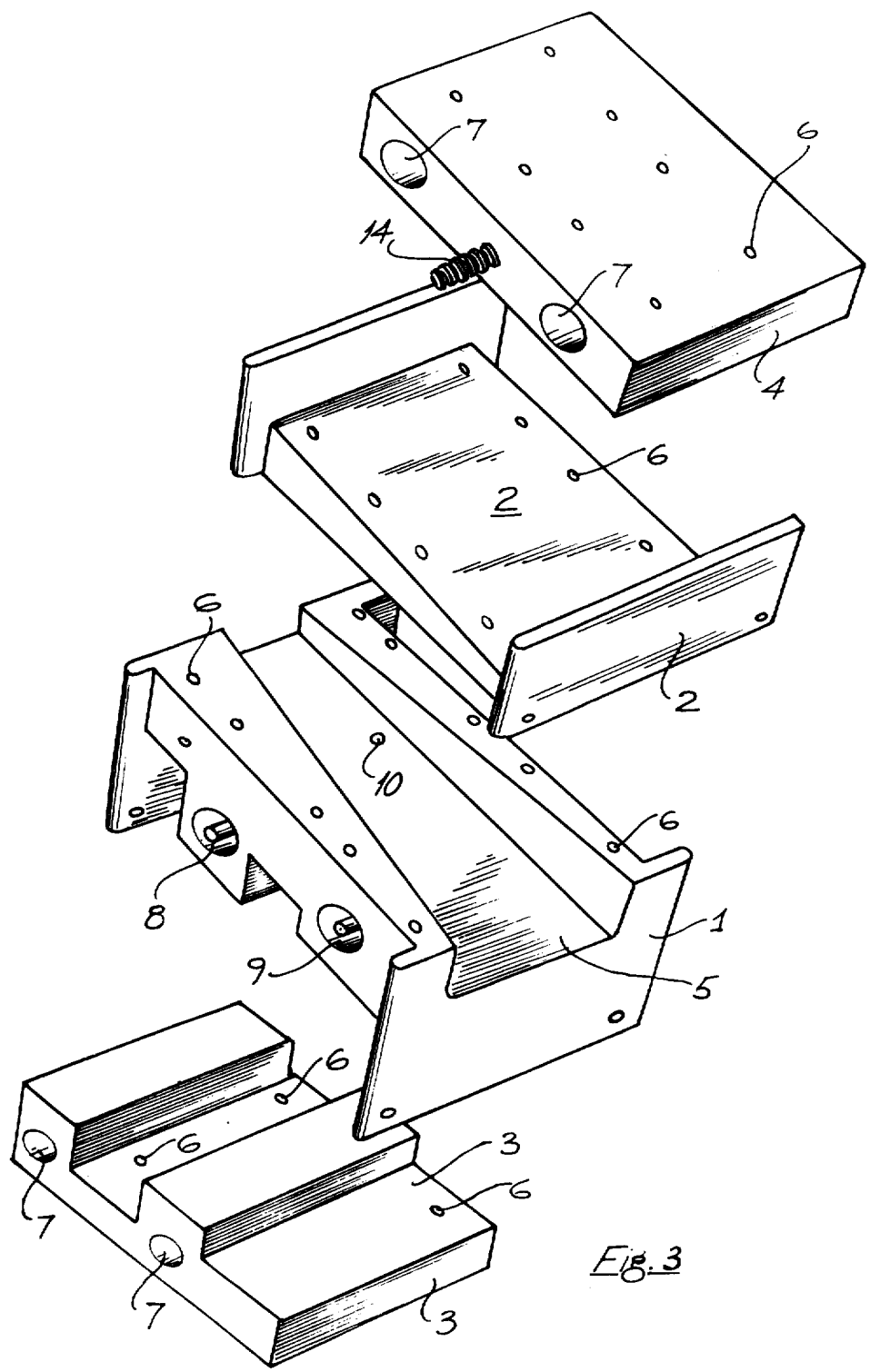
FIG. 3 is an exploded view of portion of the cell.

Referring to the drawings and initially to FIGS. 1 to 3 thereof there is provided a spectral analysis cell having a cell body which comprises a first interior body member 1, a second interior body member 2, first exterior body member 3 and a second interior body member 4. The first exterior body member 1 has a cut-out passageway which when the second interior body member 2 is bolted to it, forms an elongated interior portion 5 for the cell. This elongated interior portion 5 has it will be noted a reducing cross-sectional area from one end to the other this is chosen to conform with the optical beam of the particular spectrometer with which it will be used. These four members are bolted together by nuts and bolts and screws where appropriate through holes 6 which may or may not be threaded.

The exterior body members 3 and 4 are provided with holes 7 for the reception of heaters, not shown. The first interior body member 1 is provided with a pair of ports namely a trapping port 8 and an evacuating port 9. The trapping port 8 communicates with the interior portion 5 through a hole 10.

Figure 4:
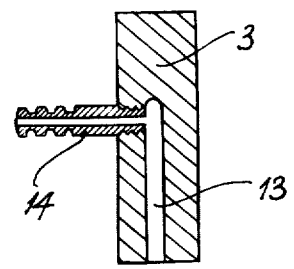
FIG. 4 is a sectional view of one portion of the cell.
Figure 5:
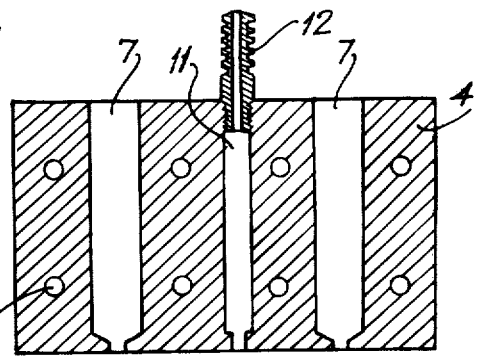
FIG. 5 is a sectional view of another portion of the cell.

Cooling ducts are provided in the two exterior body members. Referring to FIGS. 4 and 5 a cooling duct 11 is formed in the second exterior body member 4 and has fitted to it a standard inlet connection 12. A duct 13 is provided in the first exterior body member 3 and has an outlet connection 14 fitted to it. The ducts 11 and 13 are connected together by a length of suitable tubing, not shown.

Figure 6:
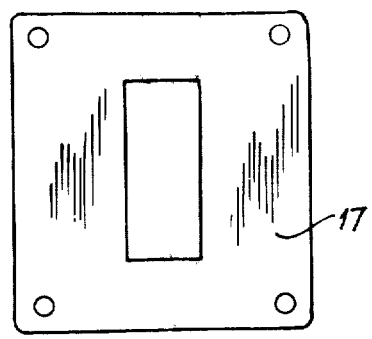
FIG. 6 is a front view of a window clamp.
Figure 7:
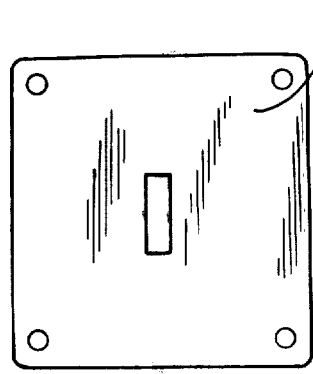
FIG. 7 is a front view of another window clamp.

Referring to FIGS. 2, 6 and 7, infrared permeable light windows 15 and 16 are mounted in position by means of a large window clamp 17 and a small window clamp 18 to the ends of the cell.

The trapping port 8 is sealed by a screw on cap 19.

A purging valve, indicated generally by the reference numeral 20, see FIG. 1 is provided and communicates with the evacuating port 9. The purging valve 20 is provided with an inlet port 21 and a hand operated control wheel 22. A cover 23 is provided.

Certain other gaskets, frame supports and the like are provided but for simplicity of understanding of the invention these have not been illustrated or described.

In use, a sample trapping tube, typically a length of ¼" OD glass tubing is used in conventional manner as a trapping device to condense and retain a fraction from a chromatograph. The usual micro-trapping techniques are available for example, the sample trapping tube may be cooled, packed with glass or silica wool or packed with an absorbent or adsorbent material, such as, for example, any suitable gas chromatography column packing. Once the fraction has been trapped in the sample trapping tube, the tube or that portion of it containing the fraction is introduced into the trapping port 8 and the cap 19 secured in position. The purging valve 20 is closed and the heaters, not shown, in the holes 7 are used to vapourise the sample which is analysed in an infrared spectrometer by passing the spectrometer "sample beam" through the cell via, windows 15 and 16.

When the spectroscopic analysis is completed the cell can be flushed out, for example, by means of an inert gas or by being evacuated through the evacuation port 9 in conventional manner by the purging valve 20.

With the present invention it has been found that the design of the shape of the interior portion 5 ensures that the vapour is almost completely confined to the optical path of the spectrometer sample beam. Further, the high transmission which is achieved with this cell facilitates the scale expansion of the spectrum and further reduces the quantity of material required to give a useful analysis. With appropriate trapping techniques the cell can be used to examine materials which have either high or low boiling points, that is to say, it can be used with the majority of materials for which gas chromatography is appropriate.

The shape of the interior tubular portion should be so arranged that its cross-sectional area at any point follows the optical beam of the particular spectrometer been used. For example, the interior body portion could have a cross-sectional area which converges from both ends to an intermediate throat.

A cell according to the present invention being used with a Perkin-Elmer 237 spectrometer and had the following characteristics with this spectrometer

| SPECIFICATION | |
|---|---|
| Cell Transmission | |
| Assembled | greater than 75% T |
| IR Windows | demountable 3mm KBr plates |
| Optical Path | 9cm long tapered stainless steel |
| Stability of Spectra | less than 3% T change in any 10 minute period after cell reaches control temperature |
| Temperature Range | 20° C. to 270° C. |
| Heating Rate | 20° C. to 270° C. in 13 minutes. |
| Cooling Rate | 270° C. to 20° C. in 8 minutes. |

It will be appreciated that the upper temperature limits are controlled by the materials used and that referably stainless steel is used on the construction of the major body portions.

Figure 8:
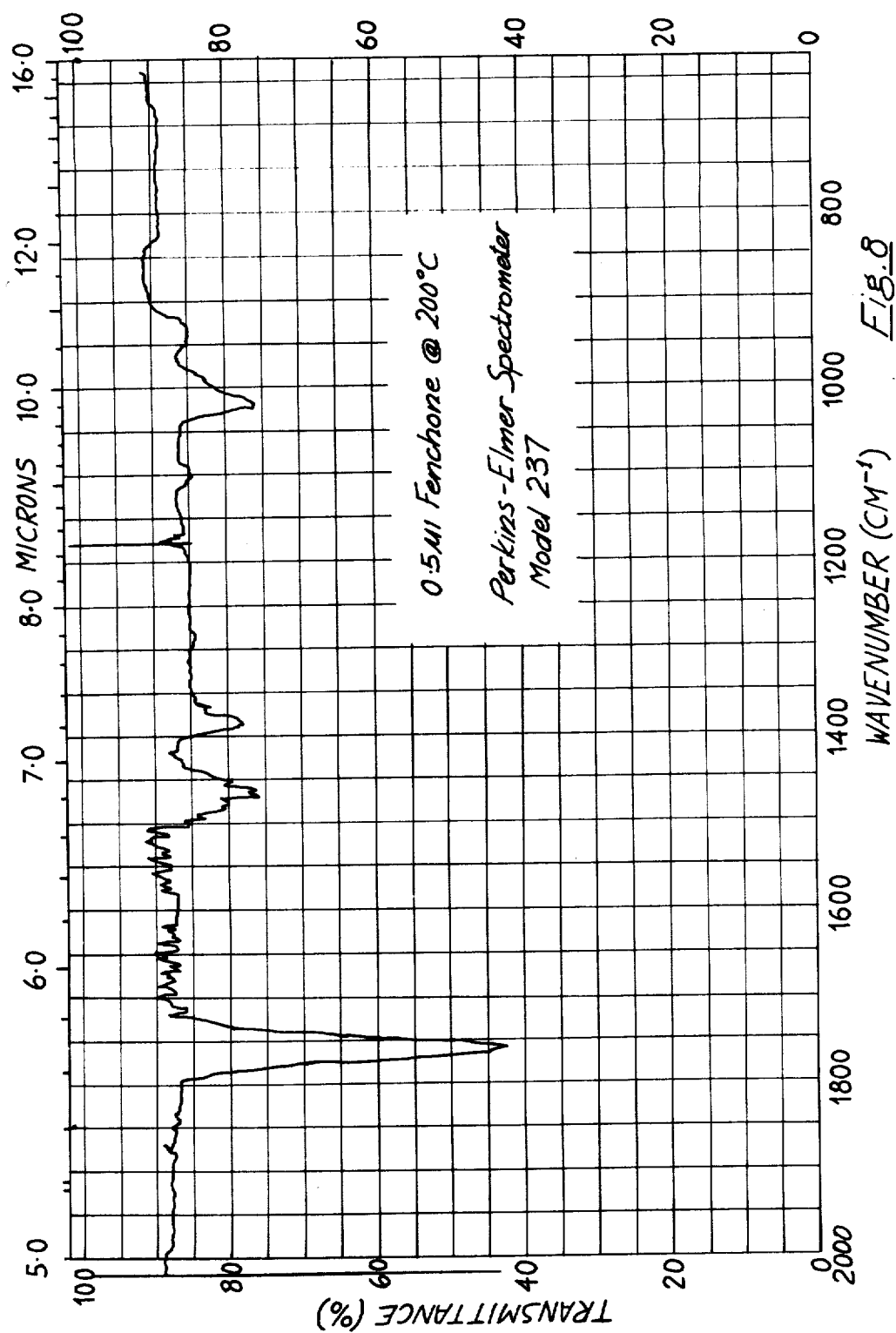
FIG. 8 is a typical graph of a result obtained according to the invention.
Figure 9:
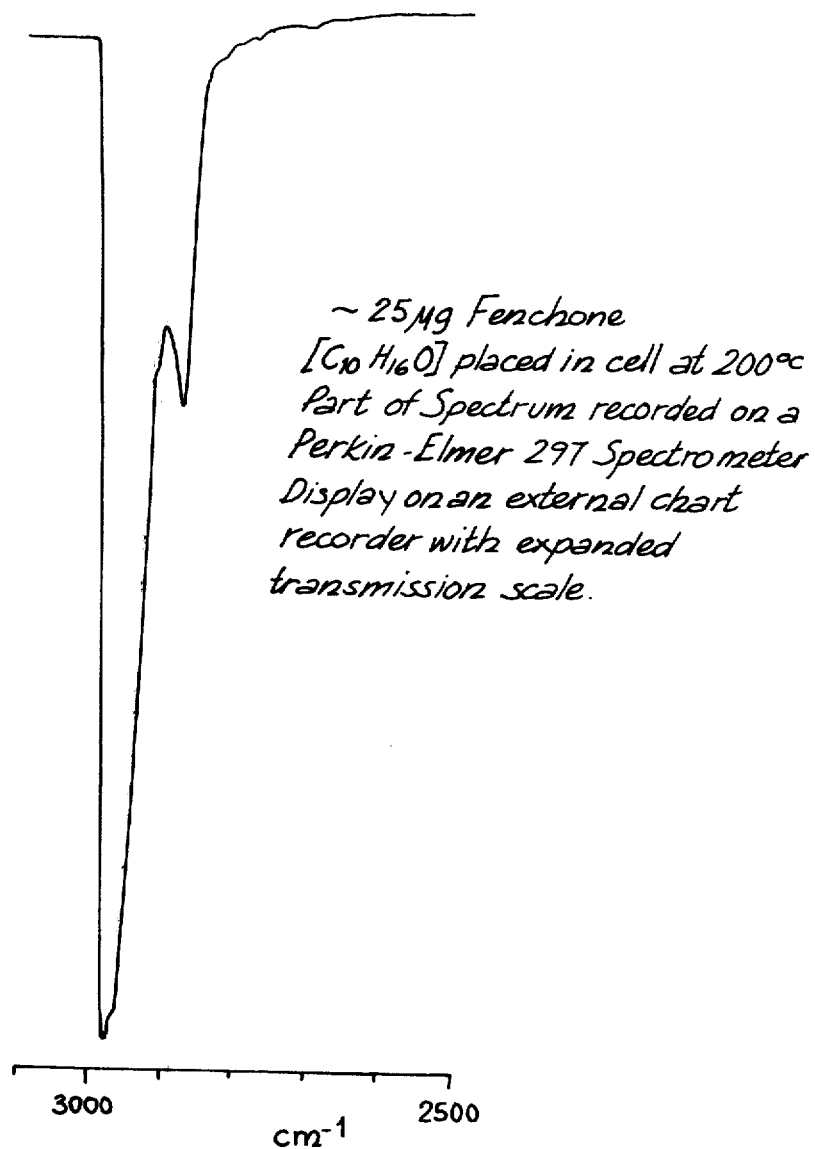
FIG. 9 is another graph of another result obtained with a cell according to the invention.

FIGS. 8 and 9 show two typical graphs of the percentage transmittance on two samples with the cell described above. The quantities and temperatures stated are only approximate. These results were obtained without using scale expansion.

Figure 10:
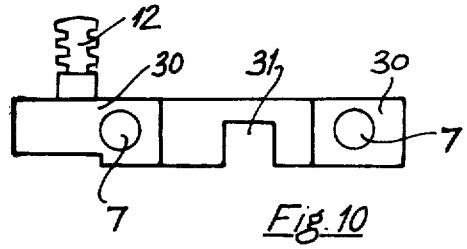
FIG. 10 is a plan view of an alternative construction of one portion of a cell according to the invention.

In the embodiment described above the sampling was carried out by using a sample trapping tube. Needless to say the sample may be introduced into the trapping chamber in the vapour state. Referring to FIG. 10 there is illustrated a plan view a modification of the first exterior member body 3, here identified by the reference numeral 30, parts similar to those described already with reference to the previous drawings being identified by the same reference numerals. In this embodiment a cooling block 31 is provided there are many such conventional cooling blocks for example those sold under the Mark PELTIER. In this case, in use, the sample is introduced into the trapping port 8 in the vapour state the interior of the trapping port 8 is cooled by the cooling device 31, thus solidifying or liquidizing the sample, the cap 19 or a shut-off valve is used to seal the trapping chamber and with the cell fitted into a spectrometer, the analysis may be performed as heretofore described.

Figure 11:
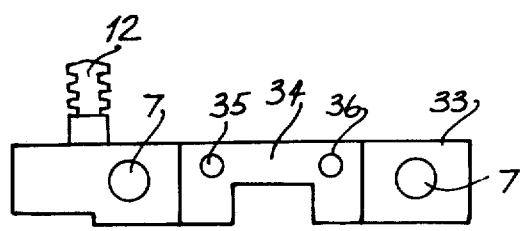
FIG. 11 is a plan view of a further modification.

FIG. 11 describes an even further alternative construction of a first exterior body member 33, parts similar to those described already being identified by the same reference numeral in this embodiment of the invention there is provided a cooling device 34 having a cooling fluid inlet port 35 and a cooling fluid outlet port 36 including cooling produced by adiabatic expansion of gases. The cooling device 34 is operated in conventional manner.

It will also be appreciated that the trapping port 8 could be so modified as to be fitted with a standard gas chromatographic injection septum (silicone rubber, PTFE faced) through which the liquid samples could be injected with standard micro syringes.

It will also be appreciated that the design of the cell is such that liquid or solid materials can be introduced into the trapping port 8 and that any vapours or gases released from these materials during heating can be examined by using the cell in a similar manner to that described above. It should be noted that all the sample does not have to be vapourised.

It will also be appreciated that the position and design details of the purging valve and trapping ports may be altered, for example, to reduce the temperature gradient within the cell when operating at a high temperature. An additional trapping port may be provided to facilitate the introduction of liquid samples as indicated above by direct injection through a PTFE faced silicone rubber septum from a micro-syringe.

It is envisaged that the upper temperature limit may be increased to 300° C. and possibly higher. It will also be appreciated that the design of the main body and in particular the interior body portion will vary depending on the type of spectrometer used.

I claim:

1. A spectral cell for the spectroscopic analysis of materials comprising in combination
a pair of elongated interior body members secured together to form an elongated tubular interior portion having an internal tapered rectangular cross-sectional area the dimensions of which are arranged to follow the optical beam of a particular spectrometer;

a trapping chamber for reception of a trapped sample integral with one of said body members;

means for communicating between said trapping chamber and said interior portion heating means incorporated in an exterior body member;

cooling means incorporated in an exterior body member;

an infrared permeable window at each end of the tubular interior portion; and an external purging means in communication with the interior of the cell.

2. A spectral analysis cell as claimed in claim 1 comprising:

a first of said pair of interior body member having a tapered internal cross-sectional cut-out area;

a second of said pair of interior body member having a flat face adapted to be bolted to the first interior body member to form a space of rectangular cross-section tapered from one end to the other to conform with the optical spectrometer beam;

said exterior body members adapted to be secured to the outsides of the two interior members;

apertures in the exterior body member for heating and cooling media;

trapping and evacuating ports commicating with the interior tapered space; and means for clamping the infrared permeable windows to the end of the cell.

3. A spectral cell for the spectroscopic analysis of materials comprising;

an interior portion and an exterior portion;

heating means on the exterior portion;

cooling means on the exterior portion;

said interior portion being of elongated tubular dimension and having a tapered rectangular cross-sectional area conforming to the optical beam of a particular spectrometer;

window means at each end of the cell and aligned with the interior portion for the passage of said optical spectrometer beam;

means for communicating with the interior portion for the introduction of materials to be analyzed; and valved external purging means communicating with the interior portion for the introduction of purging material.

* * * * *